(12) United States Patent
Han et al.

(10) Patent No.: US 12,376,809 B2
(45) Date of Patent: Aug. 5, 2025

(54) VEHICLE-MOUNTED ANGIOGRAPHY MACHINE WITH DOUBLE-ROBOTIC-ARM TYPE STRUCTURE

(71) Applicants: GENERAL HOSPITAL OF PLA NORTHERN THEATER COMMAND, Shenyang (CN); SHENYANG INSTITUTE OF AUTOMATION, CHINESE ACADEMY OF SCIENCES, Shenyang (CN)

(72) Inventors: Yaling Han, Shenyang (CN); Jingyang Sun, Shenyang (CN); Ming Liang, Shenyang (CN); Xiaozeng Wang, Shenyang (CN); Yang Li, Shenyang (CN); Dan Liu, Shenyang (CN); Hao Liu, Shenyang (CN); Peng Lin, Shenyang (CN)

(73) Assignees: GENERAL HOSPITAL OF PLA NORTHERN THEATER COMMAND, Shenyang (CN); SHENYANG INSTITUTE OF AUTOMATION, CHINESE ACADEMY OF SCIENCES, Shenyang (CN)

( * ) Notice: Subject to any disclaimer, the term of this patent is extended or adjusted under 35 U.S.C. 154(b) by 252 days.

(21) Appl. No.: 18/038,445

(22) PCT Filed: Mar. 31, 2021

(86) PCT No.: PCT/CN2021/084476
§ 371 (c)(1),
(2) Date: May 24, 2023

(87) PCT Pub. No.: WO2022/110598
PCT Pub. Date: Jun. 2, 2022

(65) Prior Publication Data
US 2023/0404497 A1    Dec. 21, 2023

(30) Foreign Application Priority Data

Nov. 24, 2020   (CN) .......................... 202011329410.2

(51) Int. Cl.
*A61B 6/00*              (2024.01)
(52) U.S. Cl.
CPC .......... *A61B 6/4405* (2013.01); *A61B 6/4458* (2013.01)
(58) Field of Classification Search
CPC ......... A61B 1/00; A61B 1/00; A61B 1/00128; A61B 1/00121; A61B 5/70; A61B 5/704;
(Continued)

(56) References Cited

U.S. PATENT DOCUMENTS

2003/0091153 A1    5/2003   Crain et al.
2006/0087746 A1*   4/2006   Lipow .................... A61B 34/37
                                                              359/689

FOREIGN PATENT DOCUMENTS

CN           2907546 Y        6/2007
CN         101428420 A         5/2009
(Continued)

*Primary Examiner* — Don K Wong
(74) *Attorney, Agent, or Firm* — Bayramoglu Law Offices LLC (57) ABSTRACT

A vehicle-mounted angiography machine with a double-robotic-arm type structure is used for interventional surgery diagnosis and treatment on patients on the site of cardiovascular diseases and on the way and occupies a small space. The vehicle-mounted angiography machine includes a six-degree-of-freedom robotic lower arm at the lower portion of an ambulance body space, a three-degree-of-freedom mobile table located in the middle of the space for moving a patient, and a seven-degree-of-freedom robotic upper arm at the upper portion of the space. An end portion of the upper arm is connected to a flat panel detector of the angiography machine, and an end portion of the lower arm is connected (Continued)

to an anode ball tube of the angiography machine, Large-scale isocentric detection is realized by cooperation of the central motion of the upper arm and the lower arm and the up-down, left-right and front-back motion of the table.

6 Claims, 12 Drawing Sheets

(58) Field of Classification Search
CPC .. A61B 5/702; A61B 6/00; A61B 6/02; A61B 6/04; A61B 6/03; A61B 6/0407; A61B 6/0487; A61B 6/42; A61B 6/44; A61B 6/4405; A61B 6/4411; A61B 6/4417; A61B 6/4429; A61B 6/4476; A61B 2090/571; A61B 90/57; A61B 90/60; A61B 90/80; A61B 34/30; A61B 34/32; A61G 2210/50; A61G 2210/00; A61G 3/00; A61G 3/001
See application file for complete search history.

(56) References Cited

FOREIGN PATENT DOCUMENTS

| | | | |
|---|---|---|---|
| CN | 206120334 U | 4/2017 | |
| CN | 107296692 A | 10/2017 | |
| CN | 107693035 A | 2/2018 | |
| CN | 209884171 U | 1/2020 | |
| CN | 210077676 U | 2/2020 | |
| CN | 112386269 A | 2/2021 | |
| EP | 0517601 A1 | 12/1992 | |
| JP | 2003038473 A | 2/2003 | |

* cited by examiner

VEHICLE-MOUNTED ANGIOGRAPHY MACHINE WITH DOUBLE-ROBOTIC-ARM TYPE STRUCTURE

CROSS REFERENCE TO THE RELATED APPLICATIONS

This application is the national phase entry of International Application No. PCT/CN2021/081476, filed on Mar. 31, 2021, which is based upon and claims priority to Chinese Patent Application No. 202011329410.2, filed on Nov. 24, 2020, the entire contents of which are incorporated herein by reference.

TECHNICAL FIELD

The present invention belongs to the technical field of medical devices, and more particularly relates to a vehicle-mounted angiography machine with a double-robotic-arm type structure.

BACKGROUND

At present, the most effective mode for the treatment of acute myocardial infarction is to adopt a percutaneous coronary intervention method to open infarction-related coronary arteries fast, however, percutaneous coronary intervention needs to be performed under the conditions of an interventional catheter room equipped with related interventional devices such as a cardiovascular angiography X-ray machine. At present, although a studied vehicle-mounted mobile shelter with the function of the interventional catheter room can deliver the devices and interventional surgeons to the patient diagnosis and treatment site, due to the large volume of a shelter system, the large deployment area before the surgery, the long deployment time and long folding time after the surgery, and unavailable "immediate" surgical rescue according to the patient condition during transportation, this kind of interventional surgery shelter cannot realize timely diagnosis and treatment for acute myocardial infarction patients in random areas.

A kind of miniaturized ambulance-type cardiovascular interventional catheter room with good mobility, high integration, strong maneuverability and fast response speed is urgently needed, which can quickly arrive at the site where patients suffer from acute myocardial infarction, can be rapidly deployed on the site to "immediately" carry out minimally invasive interventional surgery diagnosis and treatment for the patients, at the same time, has the function of performing interventional surgery at any time according to the conditions on the way to the hospital to ensure the vital signs of the patients, and has specific important application significance.

Furthermore, an angiography machine installed in a hospital interventional surgery catheter room is composed of a two-degree-of-freedom C-ring structure of apparatuses transmitting and receiving X-rays, with an installation form being roughly a ground shaft type and a suspension type, which is large in volume and weight, so as not to be easily installed in a conventional ambulance. If cardiovascular interventional surgery is required to be performed in the ambulance, it is necessary to install the angiography machine used for the cardiovascular interventional surgery in the ambulance, and thus a double-robotic-arm type vehicle-mounted angiography machine without a C-ring structure of the present invention is urgently needed, thereby reducing the structure of the whole angiography machine and satisfying a loading requirement of a narrow space in the ambulance.

SUMMARY

The present invention provides, specific to defects in the prior art, a vehicle-mounted angiography machine with a double-robotic-arm type structure, which is used for interventional surgery diagnosis and treatment on patients on the site of cardiovascular diseases and on the way, occupies a small space and solves the problem that a conventional digital subtraction angiography (DSA) occupies a large space and cannot be arranged in a mobile ambulance body.

In order to achieve the above objective, the present invention adopts the following technical solutions, including a six-degree-of-freedom robotic lower arm at the lower portion of an ambulance body space, a three-degree-of-freedom mobile table located in the middle of the space for moving a patient, and a seven-degree-of-freedom robotic upper arm at the upper portion of the space; and an end portion of the upper arm is connected to a flat panel detector of the angiography machine, and an end portion of the lower arm is connected to an anode ball tube of the angiography machine.

Large-scale isocentric detection is realized by cooperation of the central motion of the upper arm and the lower arm and the up-down, left-right and front-back motion of the table, thereby providing high-quality angiograms in the minimally invasive surgery process.

Further, both the robotic upper arm and the robotic lower arm include a six-degree-of-freedom module, the six-degree-of-freedom module of the robotic lower arm is provided with the anode ball tube, and the robotic upper arm further includes a seventh-shaft module arranged on the six-degree-of-freedom module.

Further, the six-degree-of-freedom module includes a first-second joint base, a third-joint module arranged on the first-second joint base, and a fourth-fifth-sixth-shaft module arranged on the third-joint module.

Further, the first-second joint base includes a first-shaft base and a second-shaft base arranged above the first-shaft base; the first-shaft base and the second-shaft base are connected through a crossed roller bearing, a pivot joint is rotationally connected in the first-shaft base, one end of the pivot joint penetrates through the first-shaft base, with a penetrating-out end portion connected to the bottom of the second-shaft base, the other end of the pivot joint is driven by a pivot joint drive motor to rotate, and the second-shaft base is driven by the pivot joint to rotate accordingly; the third-joint module is arranged above the second-shaft base; and a gear motor is installed on the second-shaft base, and the gear motor is installed on the second-shaft base through a motor mounting plate.

Further, the third-joint module includes a third-shaft base, and the front portion of the third-shaft base and the front portion of the second-shaft base are connected through a pivot; the gear motor drives the pivot to rotate, a gas spring is arranged between the rear portion of the second-shaft base and the rear portion of the third-shaft base, one end of the gas spring is hinged to the second-shaft base, and the other end of the gas spring is hinged to the bottom of the third-shaft base; the third-shaft base is provided with two parallel mobile guide rail and slide block modules, and a fourth-shaft base is in sliding connection to the third-shaft base through the bidirectional mobile guide rail and slide block modules; the third-shaft base is provided with a rack, and the fourth-shaft base is provided with two gears: a first gear and a second gear; both the first gear and a first pulley are installed on a first third-shaft and are coaxial, and a second pulley, the second gear and a third pulley are all installed on a second third-shaft and are coaxial; the first third-shaft is connected to the fourth-shaft base through a first mounted bearing, and the second third-shaft is connected to the fourth-shaft base through a second mounted bearing; the first pulley and the third pulley are connected through a synchronous belt to form a first synchronous belt transmission structure; the fourth-shaft base is provided with a third-shaft joint module motor, a motor shaft of the module motor is provided with a fourth pulley, and the fourth pulley and the second pulley constitute a second synchronous belt transmission structure through a synchronous belt; the module motor acts, the second pulley rotates and drives the second gear and the third pulley coaxial thereto to rotate together, the first pulley rotates through the first synchronous belt transmission structure to drive the first gear coaxial thereto to rotate, both the first gear and the second gear are in meshing transmission with the rack to drive the fourth-shaft base to horizontally move along the guide rail and slide block modules.

Further, the bidirectional mobile guide rail module includes a first-layer guide rail and a second-layer guide rail, where the first-layer guide rail is arranged on the third-shaft base to be connected to the third-shaft base; and a first-layer slide block is in sliding connection to the first-layer guide rail, the bottom of a guide rail connector is arranged on the upper surface of the first-layer slide block, the upper surface of the guide rail connector is provided with the second-layer guide rail, the second-layer guide rail is connected to a second-layer slide block, and the second-layer slide block is connected to the fourth-shaft base.

Further, the second gear is located between the second pulley and the third pulley, and the third-shaft joint module motor is installed on the fourth-shaft base through a third-shaft joint module motor base.

Further, the fourth-shaft base is provided with a fourth-fifth-sixth-shaft module which includes a fourth-shaft module, a fifth-shaft module and a sixth-shaft module; the fourth-shaft module includes a synchronous belt structure constituted by a first fourth-shaft pulley and a second fourth-shaft pulley, and the first fourth-shaft pulley of the synchronous belt structure is driven by a fourth-shaft motor; and the second fourth-shaft pulley serves as a driven pulley to be installed on a fourth-shaft driven shaft, and the fourth-shaft driven shaft is fixed to a fourth-shaft holder through a fourth-shaft mounted bearing, and is further connected to one side of a fifth-shaft connector; (the fourth-shaft motor drives the first fourth-shaft pulley to rotate, and the fourth-shaft driven shaft is driven by a synchronous belt to rotate, so that the fifth-shaft connector arranged on the driven shaft rotates accordingly).

The fifth-shaft module includes a synchronous belt structure constituted by a first fifth-shaft pulley and a second fifth-shaft pulley, and the first fifth-shaft pulley of the synchronous belt structure is driven by a fifth-shaft motor; the second fifth-shaft pulley serves as a driven pulley to be installed on a fifth-shaft driven shaft, and the fifth-shaft driven shaft is fixed to a fifth-shaft holder through a fifth-shaft mounted bearing, and is further connected to the other side of the fifth-shaft connector; and the fifth-shaft driven shaft is further provided with a first fifth-shaft gear, the first fifth-shaft gear is connected to a second fifth-shaft gear through meshing transmission, the second fifth-shaft gear (a bevel gear) is installed on a fifth-shaft gear shaft, and the fifth-shaft gear shaft is installed on the fifth-shaft connector through a fifth-shaft crossed roller bearing.

Further, in the robotic lower arm, the fifth-shaft crossed roller bearing is connected to the anode ball tube through a connecting rod. (The fifth-shaft motor drives the first fifth-shaft pulley to rotate, the fifth-shaft driven shaft is driven by a synchronous belt to rotate, so that the fifth-shaft connector installed on the driven shaft rotates accordingly) the fourth-shaft motor is matched with the fifth-shaft motor to synchronously move, thereby realizing the pitching motion of the fifth-shaft connector (the ball tube); and when the fifth-shaft motor independently moves, the pulley is driven to transmit the motion to the second fifth-shaft gear (realizing the sidesway motion of the ball tube).

Further, the sixth-shaft module includes a sixth-shaft holder installed on a crossed roller bearing, a sixth-shaft screw is fixed to the sixth-shaft holder, a sixth-shaft nut (a sixth-shaft screw nut) is fixed to the sixth-shaft screw, the sixth-shaft nut is connected to a sixth-shaft adapter, the sixth-shaft adapter is arranged on a sixth-shaft slide block, the sixth-shaft slide block is in sliding connection to a sixth-shaft guide rail, the sixth-shaft guide rail is arranged on the sixth-shaft holder, and the sixth-shaft screw can rotate relative to the sixth-shaft holder and is parallel to the sixth-shaft guide rail; one end portion of the sixth-shaft screw is provided with a first sixth-shaft pulley, the first sixth-shaft pulley and a second sixth-shaft pulley constitute a synchronous belt structure, the synchronous belt structure is driven by a sixth-shaft motor, and the sixth-shaft motor is fixed to the sixth-shaft holder through a sixth-shaft motor base.

Further, the fourth-shaft motor is installed on a fourth-shaft motor base, and the fifth-shaft motor is installed on a fifth-shaft motor base.

Further, in the robotic upper arm, the sixth-shaft nut is connected to a receiving panel through a seventh-shaft holder, one end of the seventh-shaft holder is connected to the sixth-shaft nut, and the other end of the seventh-shaft holder is provided with the receiving panel (the flat panel detector); the lower end of the receiving panel is rotationally connected to the seventh-shaft holder through a seventh-shaft driven shaft, the seventh-shaft driven shaft is rotationally connected to the seventh-shaft holder through a seventh-shaft crossed roller bearing, an end portion of the driven shaft is externally provided with a second bevel gear, the second bevel gear is connected to a first bevel gear through meshing transmission, the first bevel gear is installed outside a motor shaft of a seventh-shaft motor, and the seventh-shaft motor is installed on the seventh-shaft holder through a seventh-shaft motor base.

Compared with the prior art, the present invention has the beneficial effects.

By means of the structure designed in the present invention, according to a treat and cure method, a catheter room is transported beside the patient to perform emergency rescue, thereby saving patient transportation time, and realizing a better rescue effect.

The design structure in the present invention occupies a small space and solves the problem that under the conditions of movement/field operation, the conventional DSA occupies the large space and cannot be arranged in the mobile ambulance body.

Compared with a conventional C-arm, the design structure in the present invention is lighter in weight and more flexible in movement.

BRIEF DESCRIPTION OF THE DRAWINGS

The present invention is further described below with reference to the accompanying drawings and specific implementations. The scope of protection of the present invention is not limited to the expression of the following content.

In the figures, 1—upper arm. 2—lower arm, 3—mobile table. 4—first-shaft base, crossed roller bearing, 6—second-shaft base, 7—gas spring, 8—third—shaft base, 9—pivot joint, 10—second-shaft gear motor;

51—first guide rail module, 52—fourth-shaft base, 53—second guide rad module, 55—third-shaft rack, 56—first third-joint gear, 57—first third-shaft, 58—first third-joint pulley, 519—first mounted bearing, 510—second third joint pulley, 511—second third-joint gear, 512—second mounted bearing, 513—third third-joint pulley, 514—fourth third-joint pulley, 515—second third-shaft, 516—third-shaft joint module motor;

61—guide rail connector, 62—first-layer slide block, 64—first-layer guide rail, 65—second-layer guide rail, 66—second-layer slide block;

71—first fifth-shaft pulley, 72—first fourth-shaft pulley, 75—fifth-shaft driven shaft, 76—second fifth-shaft pulley, 77—fifth-shaft mounted bearing, 78—first fifth-shaft gear, 78—first fifth-shaft gear, 79—fifth-shaft connector, 710—second fifth-shaft gear, 711—fifth-shaft crossed roller bearing, 712—fifth-shaft gear shaft, 713—fourth-shaft mounted bearing, 714—fourth-shaft holder, 715—fourth-shaft driven shaft, 716—second fourth-shaft pulley;

81— sixth-shaft holder, 83—sixth-shaft nut, 84—sixth-shaft adapter, 85—sixth-shaft screw, 86—first sixth-shaft pulley, 87—second sixth-shaft pulley, 88—sixth-shaft motor base, 89—sixth-shaft motor, 810—sixth-shaft, guide rail, 811—sixth-shaft slide block;

91—seventh-shaft holder, 93—seventh-shaft motor, 94—first bevel gear, 95—seventh-shaft motor base, 96—seventh-shaft roller bearing, 97—receiving panel, 98—seventh-shaft driven shaft, and 99—second bevel gear.

DETAILED DESCRIPTION OF THE EMBODIMENTS

As shown in FIGS. 1 to 10, the present invention includes a six-degree-of-freedom robotic lower arm located at the lower portion of an ambulance body space, a three-degree-of-freedom mobile table located in the middle of the space for moving a patient, and a seven-degree-of-freedom robotic upper arm at the upper portion of the space.

Figure 1:
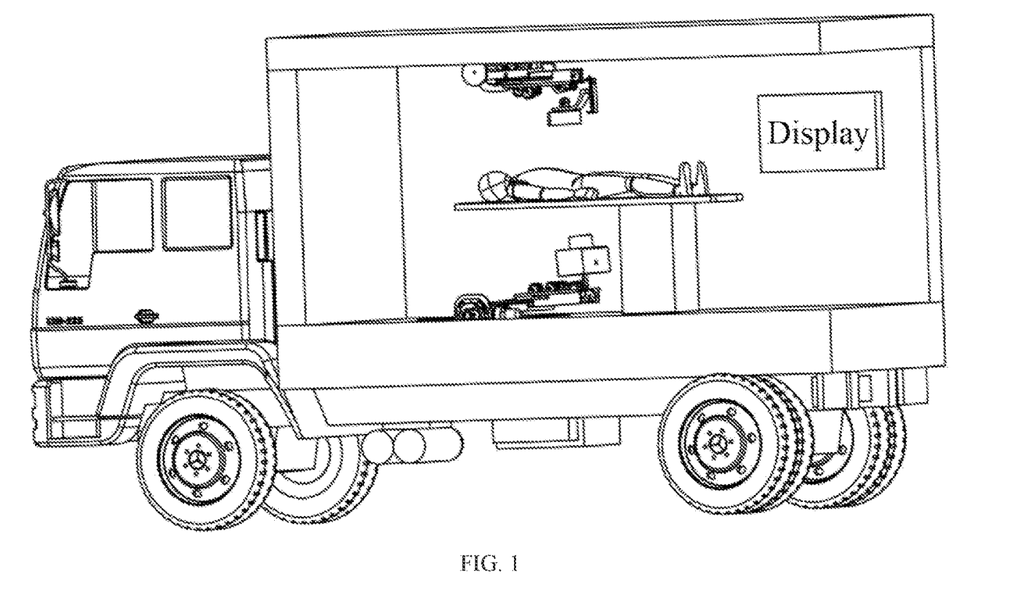
FIGS. 1 to 2 are overall schematic structural diagrams according to the present invention.
Figure 2:
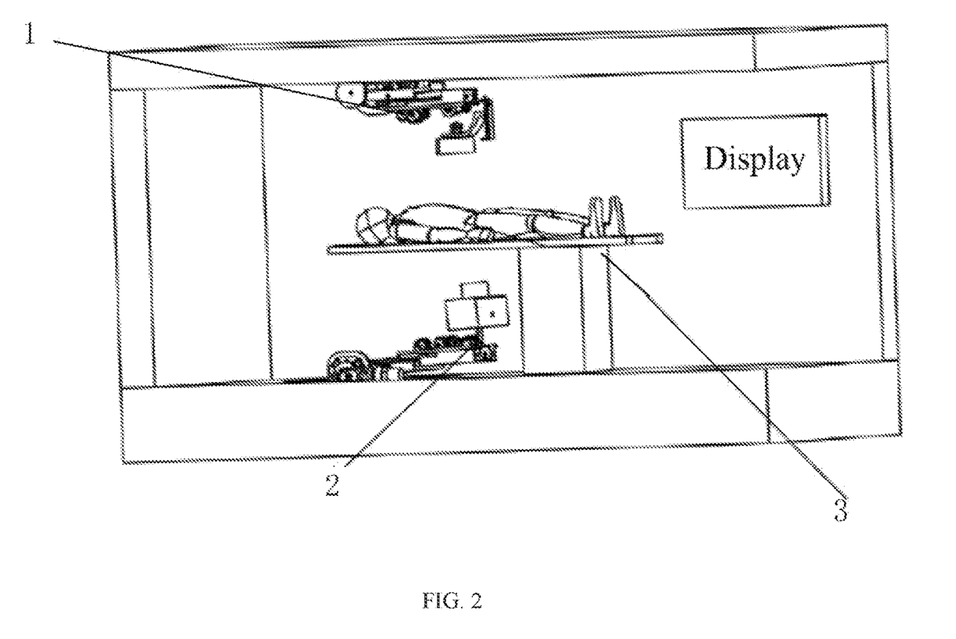

An end portion of the upper arm is connected to a flat panel detector of an angiography machine, and an end portion of the lower arm is connected to an anode ball tube of the angiography machine.

Large-scale isocentric detection is realized by cooperation of the central motion of the upper arm and the lower arm and the up-down, left-right and front-back motion of the table, thereby providing high-quality angiograms in the minimally invasive surgery process.

Figure 3A:
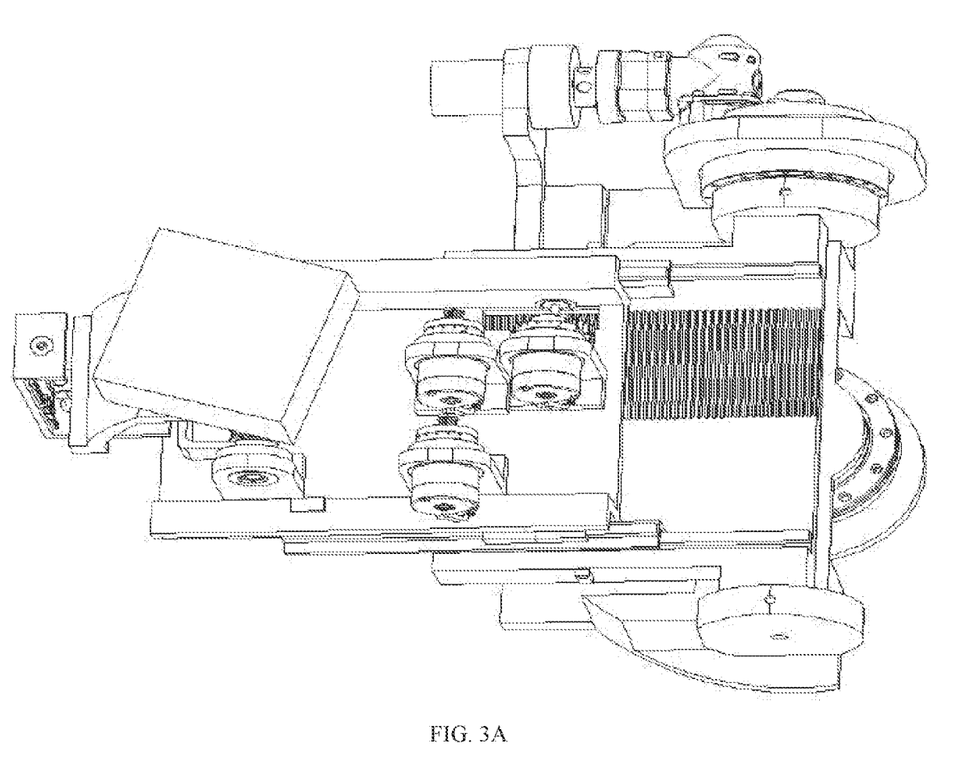
FIG. 3A is an overall schematic structural diagram of an upper arm according to the present invention.
Figure 3B:
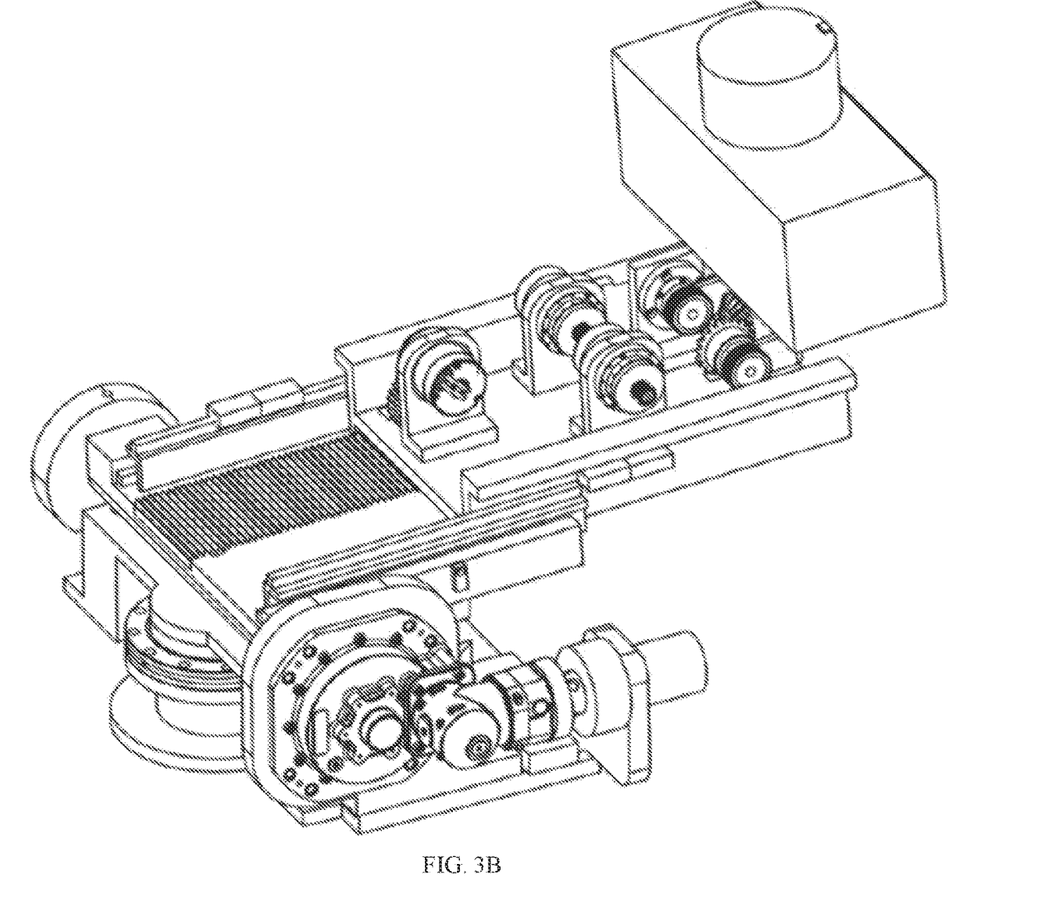
FIG. 3B is an overall schematic structural diagram of a lower arm according to the present invention.

Preferably, both the robotic upper arm and the robotic lower arm include a six-degree-of-freedom module, the six-degree-of-freedom module of the robotic lower arm is provided with the anode ball tube, and the robotic upper arm further includes a seventh-shaft module arranged on the six-degree-of-freedom module.

More preferably, the six-degree-of-freedom module includes a first-second joint base, a third-joint module arranged on the first-second joint base, and a fourth-fifth-sixth-shaft module arranged on the third-joint module.

Figure 4:
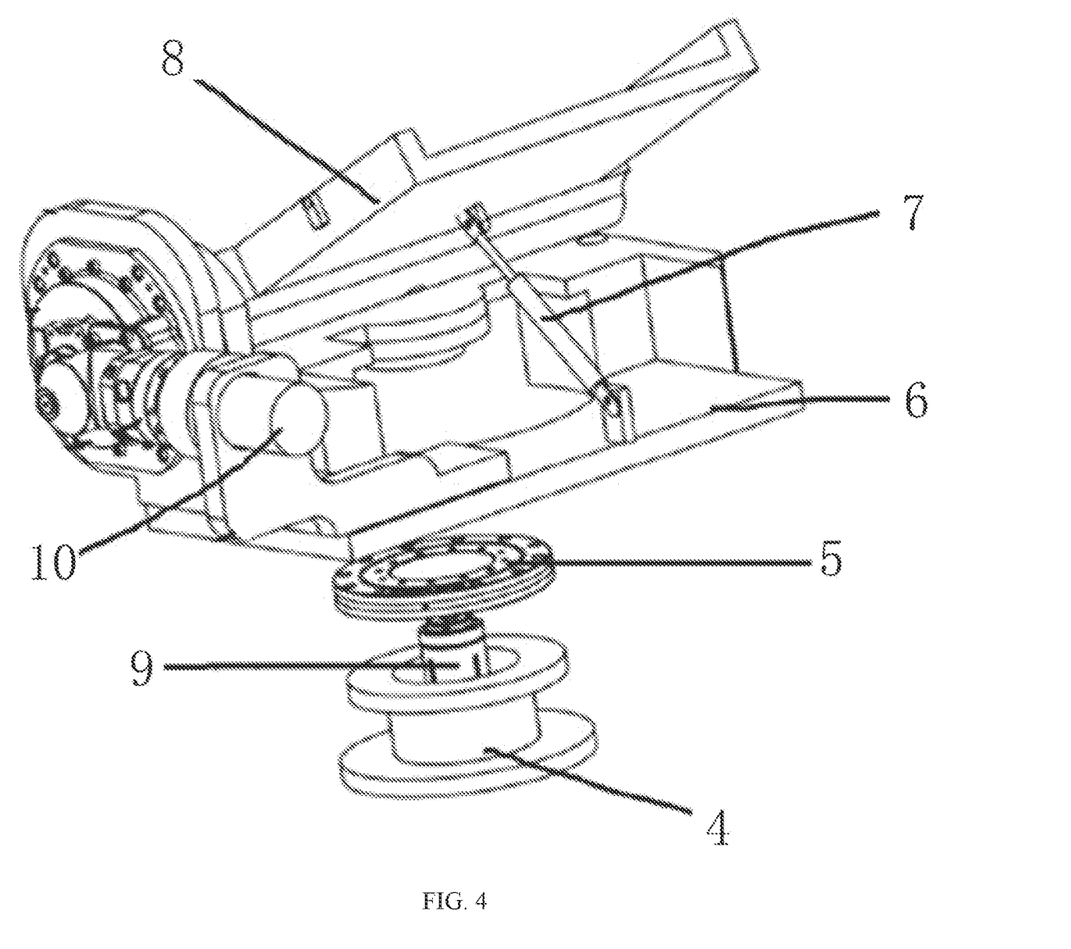
FIG. 4 is a schematic diagram of a first joint and a second joint of an upper arm and a lower arm according to the present invention.

More preferably, the first-second joint base includes a first-shaft base and a second-shaft base arranged above the first-shaft base; the first-shaft base and the second-shaft base are connected through a first-shaft crossed roller bearing, a pivot joint is rotationally connected in the first-shaft base, one end of the pivot joint penetrates through the first-shaft base, with a penetrating-out end portion connected to the bottom of the second-shaft base, the other end of the pivot joint is driven by a pivot joint drive motor to rotate, and the second-shaft base is driven by the pivot joint to rotate accordingly; the third-joint module is arranged above the second-shaft base; and a second-shaft gear motor is installed on the second-shaft base, and the gear motor is installed on the second-shaft base through a motor mounting plate.

More preferably, the third-joint module includes a third-shaft base, and the front portion of the third-shaft base and the front portion of the second-shaft base are connected through a pivot; the gear motor drives the pivot to rotate, a gas spring is arranged between the rear portion of the second-shaft base and the rear portion of the third-shaft base, one end of the gas spring is hinged to the second-shaft base, and the other end of the gas spring is hinged to the bottom of the third-shaft base; the third-shaft base is provided with two parallel mobile guide rail and slide block modules, and a fourth-shaft base is in sliding connection to the third-shaft base through the bidirectional mobile guide rail and slide block modules; the third-shaft base is provided with a third-shaft rack, and the fourth-shaft base is provided with two gears: a first third-joint gear and a second third-joint gear; both the first third-joint gear and a first third-joint pulley are installed on a first third-shaft and are coaxial, and a second third-joint pulley, the second third joint gear and a third third-joint pulley are all installed on a second third-shaft and are coaxial; the first third-shaft is connected to the fourth-shaft base through a first mounted bearing, and the second third-shaft is connected to the fourth-shaft base through a second mounted bearing; the first third-joint pulley and the third third-joint pulley are connected through a synchronous belt to form a first synchronous belt transmission structure; the fourth-shaft base is provided with a third-shaft joint module motor, a motor shaft of the module motor is provided with a fourth third-joint pulley, and the fourth third joint pulley and the second third-joint pulley constitute a second synchronous belt transmission structure through a synchronous belt; the module motor acts, the second third-joint pulley rotates and drives the second third-joint gear and the third third-joint pulley coaxial thereto to rotate together, the first third-joint pulley rotates through the first synchronous belt transmission structure to drive the first third-joint gear coaxial thereto to rotate, both the first third-joint gear and the second third-joint gear are in meshing transmission with the rack to drive the fourth-shaft base to horizontally move along the guide rail and slide block modules.

Figure 6A:
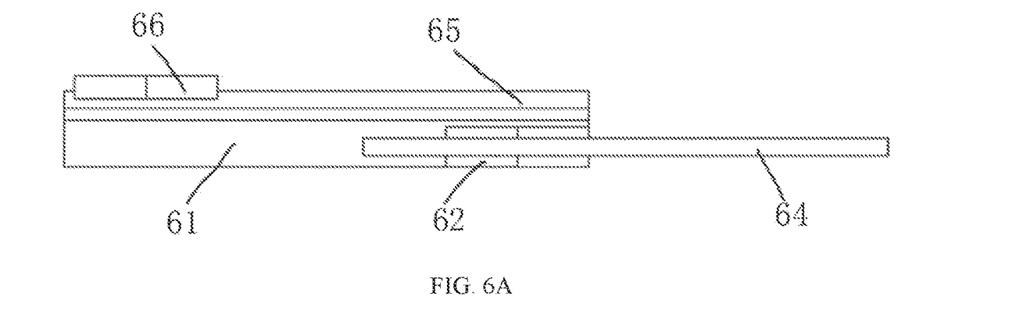
FIGS. 6A to 6C are schematic diagrams of a bidirectional mobile guide rail module according to the present invention.
Figure 6B:
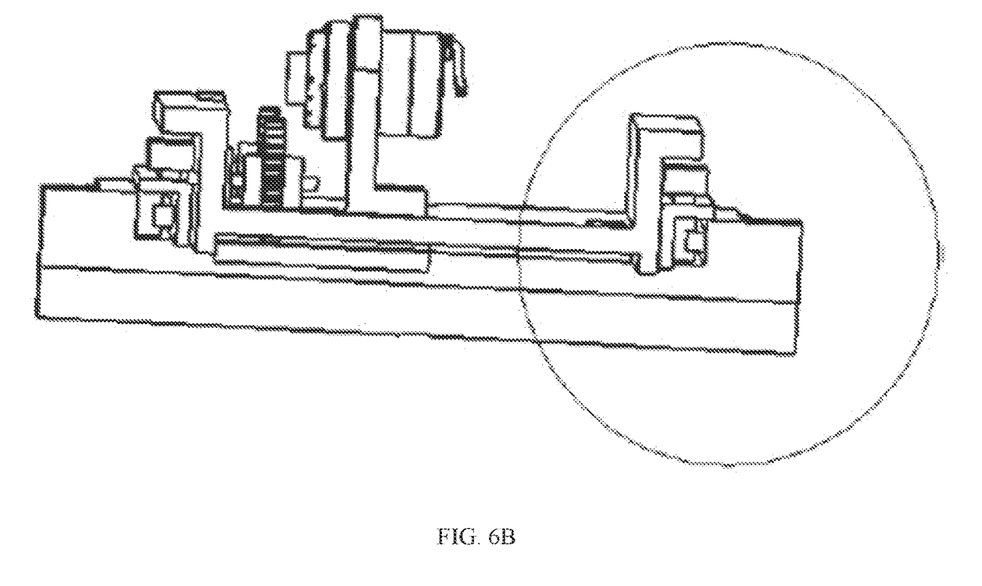
Figure 6C:
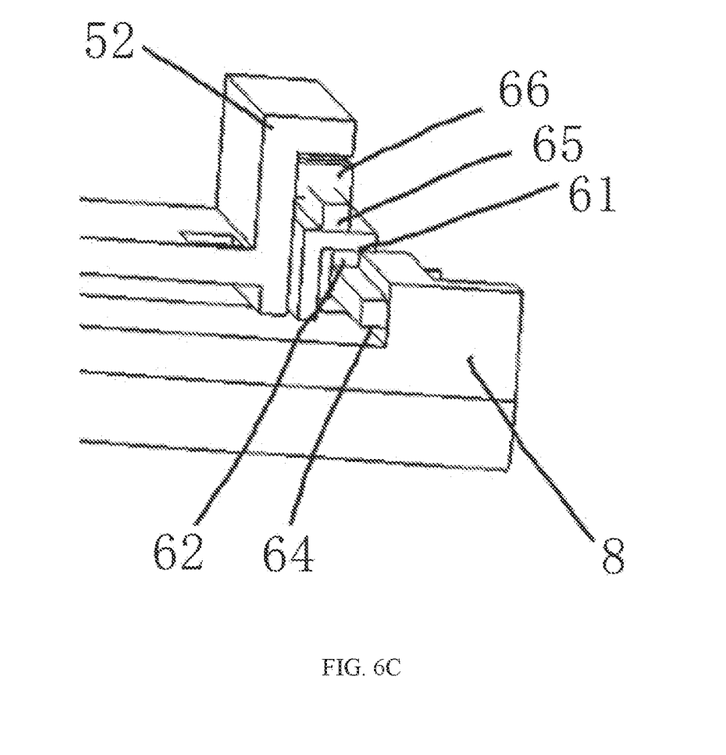

More preferably, the bidirectional mobile guide rail module includes a first-layer guide rail and a second-layer guide rail, where the first-layer guide rail is arranged on the third-shaft base to be connected to the third-shaft base; and a first-layer slide block is in sliding connection to the first-layer guide rail, the bottom of a guide rail connector is arranged on the upper surface of the first-layer slide block, the upper surface of the guide rail connector is provided with the second-layer guide rail, the second-layer guide rail is connected to a second-layer slide block, and the second-layer slide block is connected to the fourth-shaft base.

More preferably, the second gear is located between the second pulley and the third pulley, and the third-shaft joint module motor is installed on the fourth-shaft base through a third-shaft joint module motor base.

Figure 7A:
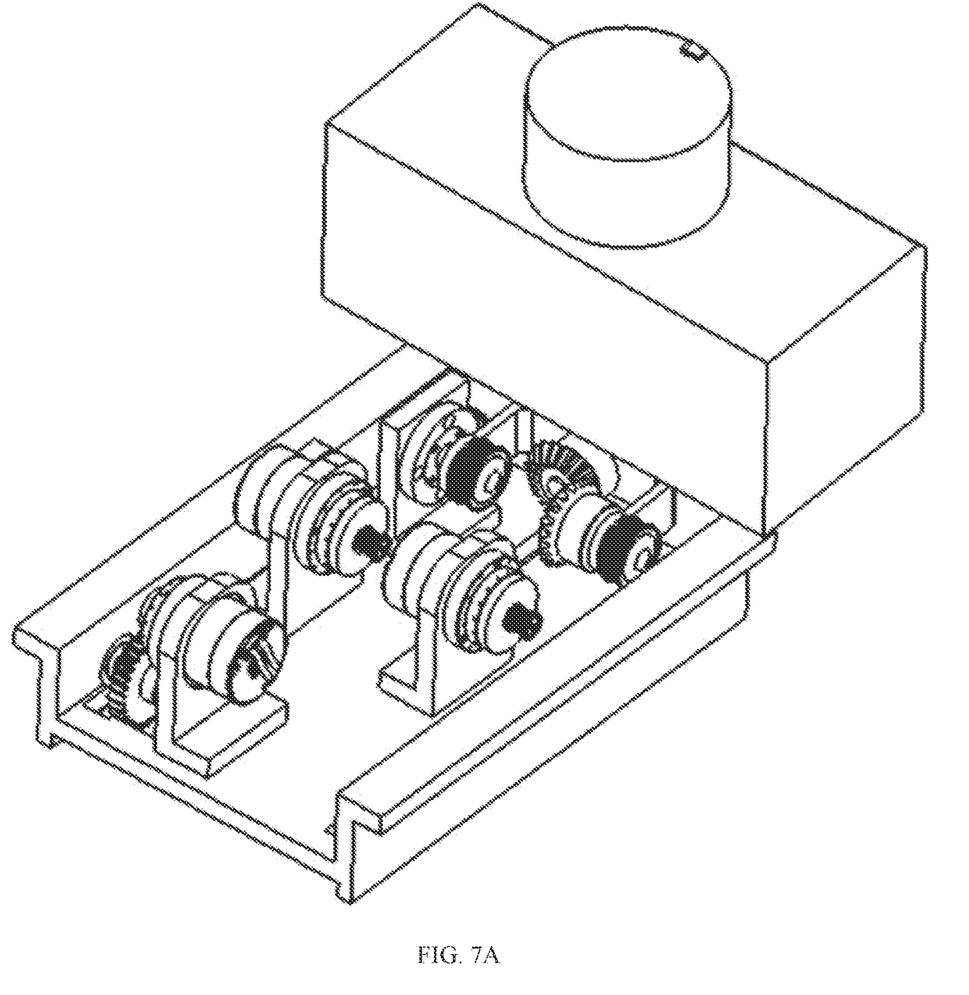
FIGS. 7A to 7B are schematic diagrams of a fourth shaft, a fifth shaft and a sixth shaft of a lower arm.
Figure 7B:
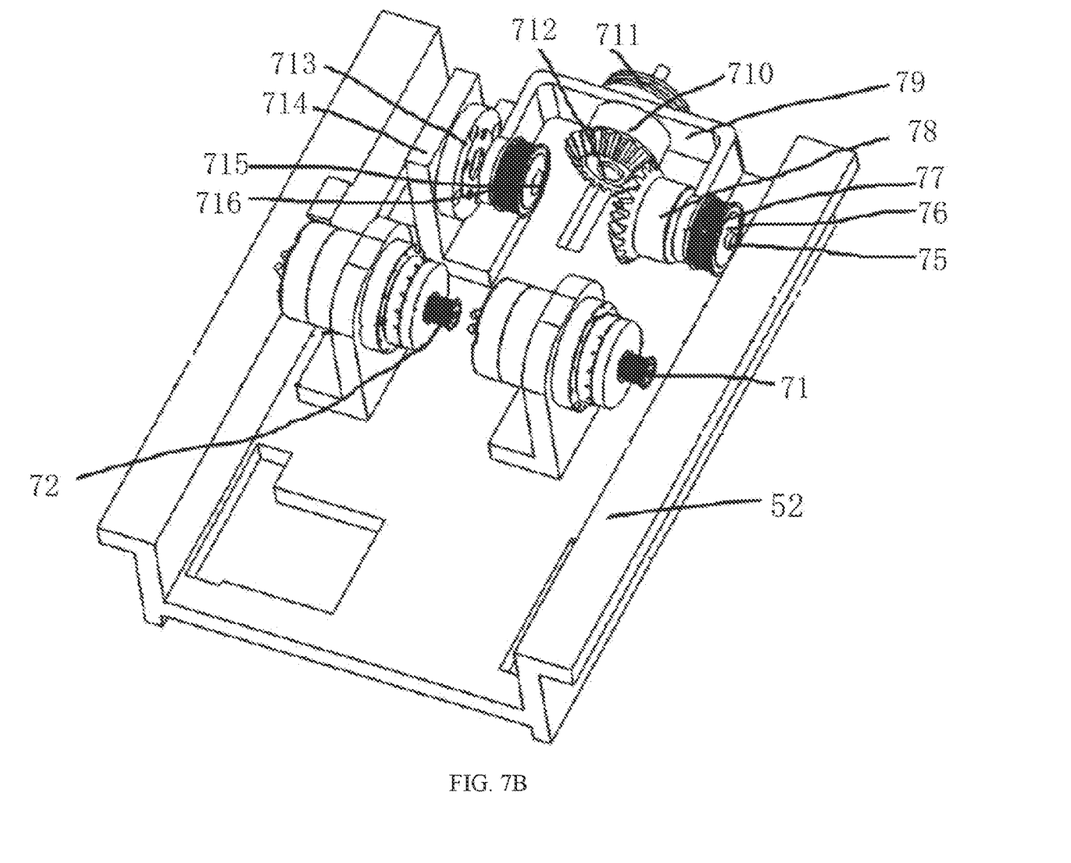
Figure 8:
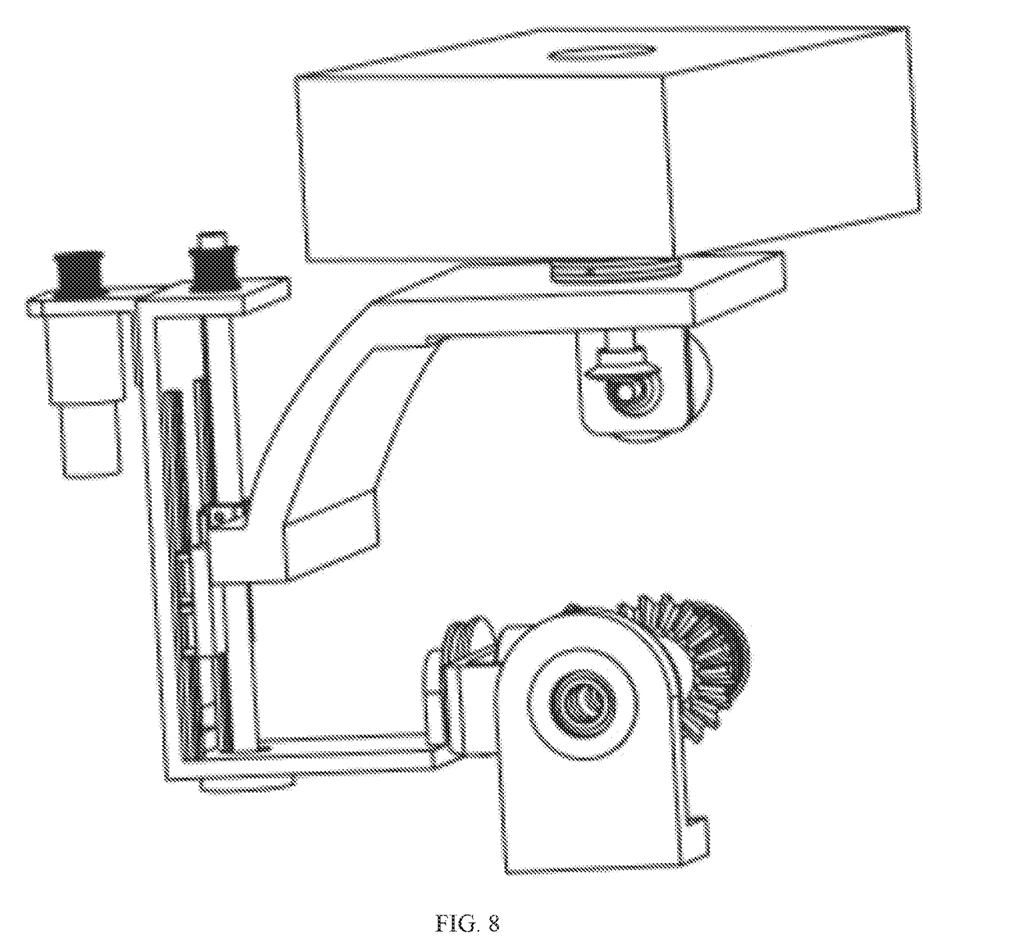
FIG. 8 is a structural schematic diagram of a sixth shaft and a seventh shaft of an upper arm.

More preferably, the fourth-shaft base is provided with a fourth-fifth-sixth-shaft module which includes a fourth-shaft module, a fifth-shaft module and a sixth-shaft module;

the fourth-shaft module includes a synchronous belt structure constituted by a first fourth-shaft pulley and a second fourth-shaft pulley, and the first fourth-shaft pulley of the synchronous belt structure is driven by a fourth-shaft motor; and the second fourth-shall pulley serves as a driven pulley to be installed on a fourth-shaft driven shaft, and the fourth-shaft driven shaft is fixed to a fourth-shaft holder through a fourth-shaft mounted bearing, and is further connected to one side of a fifth-shaft connector; (the fourth-shaft motor drives the first fourth-shaft pulley to rotate, and the fourth-shaft driven shaft is driven by a synchronous belt to rotate, so that the fifth-shaft connector arranged on the driven shaft rotates accordingly).

The fifth-shaft module includes a synchronous belt structure constituted by a first fifth-shaft pulley and a second fifth-shaft pulley, and the first fifth-shaft pulley of the synchronous belt structure is driven by a fifth-shaft motor; the second fifth-shaft pulley serves as a driven pulley to be installed on a fifth-shaft driven shaft, and the fifth-shaft driven shaft is fixed to a fifth-shaft holder through a fifth-shaft mounted bearing, and is further connected to the other side of the fifth-shaft connector;

the fifth-shaft driven shaft is further provided with a first fifth-shaft gear, the first fifth-shaft gear is connected to a second fifth-shaft gear through meshing transmission, the second fifth-shaft gear (a bevel gear) is installed on a fifth-shaft gear shaft, and the fifth-shaft gear shaft is installed on the fifth-shaft connector through a fifth-shaft crossed roller bearing.

More preferably, in the robotic lower arm, the fifth-shaft crossed roller bearing is connected to the anode ball tube through a connecting rod. (The fifth-shaft motor drives the first fifth-shaft pulley to rotate, the fifth-shaft driven shaft is driven by a synchronous belt to rotate, so that the fifth-shaft connector installed on the driven shaft rotates accordingly;) the fourth-shaft motor is matched with the fifth-shall motor to synchronously move, thereby realizing the pitching motion of the fifth-shaft connector (the ball tube); and when the fifth-shaft motor independently moves, the pulley is driven to transmit the motion to the second fifth-shaft gear (realizing the sidesway motion of the ball tube).

Figure 9:
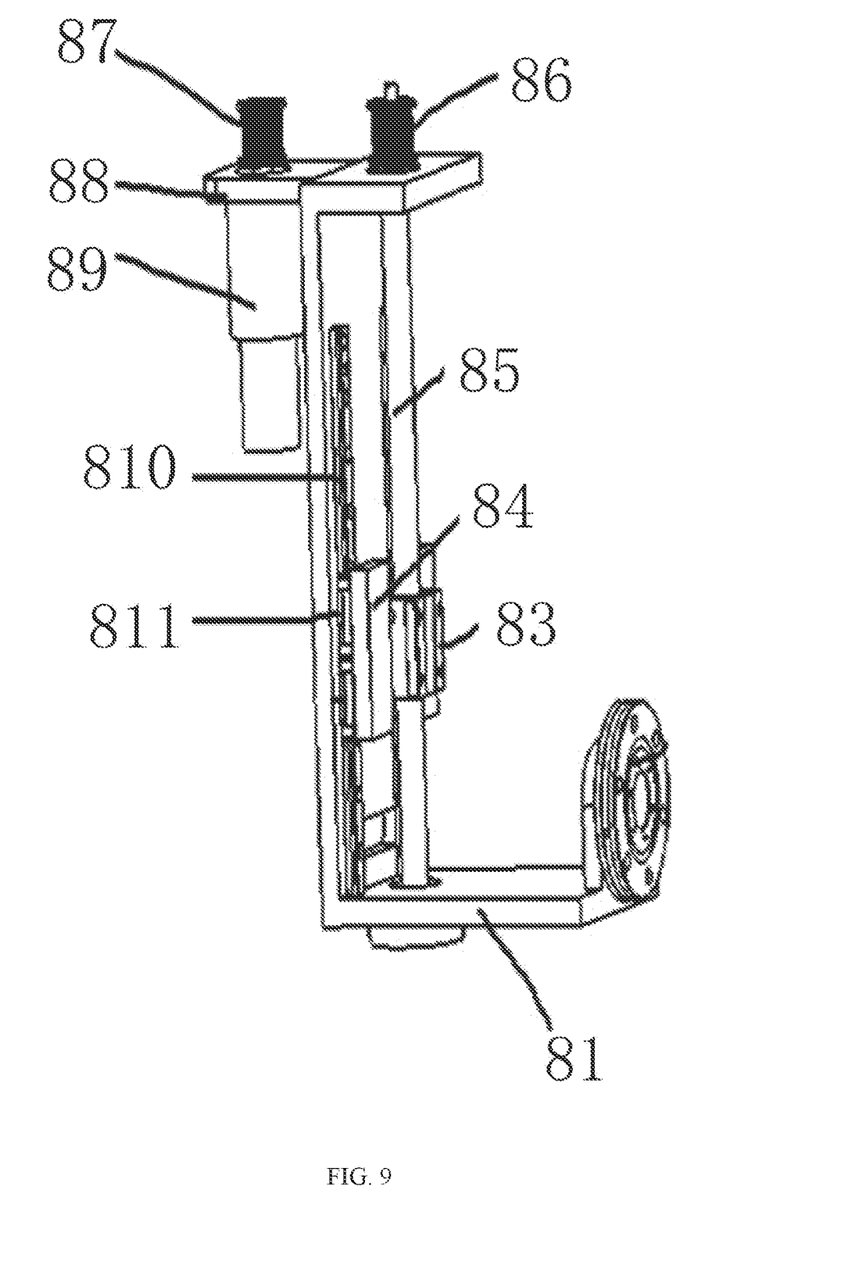
FIG. 9 is a structural schematic diagram of the sixth shaft in FIG. 8.

More preferably, the sixth-shaft module includes a sixth-shaft holder installed on a crossed roller bearing, a sixth-shaft screw is fixed to the sixth-shaft holder, a sixth-shaft nut (a sixth-shaft screw nut)is fixed to the sixth-shaft screw, the sixth-shaft nut is connected to a sixth-shaft adapter, the sixth-shaft adapter is arranged on a sixth-shaft slide block, the sixth-shaft slide block is in sliding connection to a sixth-shaft guide rail, the sixth-shaft guide rail is arranged on the sixth-shaft holder, and the sixth-shaft screw can rotate relative to the sixth-shaft holder and is parallel to the sixth-shaft guide rail; one end portion of the sixth-shaft screw is provided with a first sixth-shaft pulley, the first sixth-shaft pulley and a second sixth-shaft pulley constitute a synchronous belt structure, the synchronous belt structure is driven by a sixth-shaft motor, and the sixth-shaft motor is fixed to the sixth-shaft holder through a sixth-shaft motor base.

More preferably, the fourth-shaft motor is installed on a fourth-shaft motor base, and the fifth-shaft motor is installed on a fifth-shaft motor base.

Figure 10:
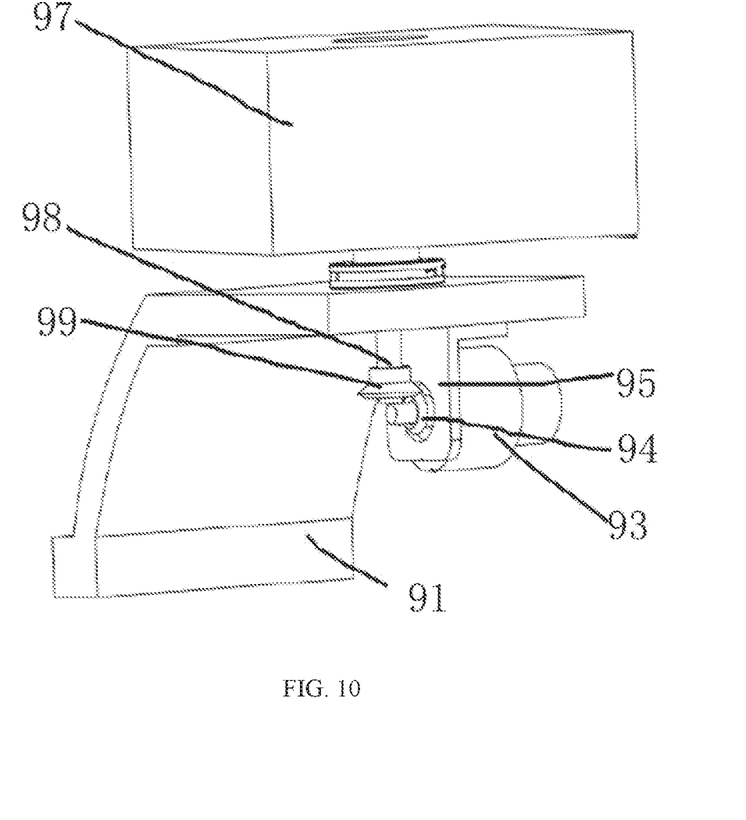
FIG. 10 is a structural schematic diagram of the seventh shaft in FIG. 8.

More preferably, in the robotic upper arm, the sixth-shaft nut is connected to a receiving panel through a seventh-shaft holder, one end of the seventh-shaft holder is connected to the sixth-shaft nut, and the other end of the seventh-shaft holder is provided with the receiving panel (the flat panel detector); the lower end of the receiving panel is rotationally connected to the seventh-shaft holder through a seventh-shaft driven shaft, the seventh-shaft driven shaft is rotationally connected to the seventh-shaft holder through a seventh-shaft crossed roller bearing, an end portion of the driven shaft is externally provided with a second bevel gear, the second bevel gear is connected to a first bevel gear through meshing transmission, the first bevel gear is installed outside a motor shaft of a seventh-shaft motor, and the seventh-shaft motor is installed on the seventh-shaft holder through a seventh-shaft motor base.

As a kind of specific embodiment:

A robot is integrally of an upper-lower double arm structure, an upper arm has seven degrees of freedom, and a lower arm has six degrees of freedom. A connection relationship of each degree of freedom is illustrated. The upper arm has seven degrees of freedom, with an end portion fixedly provided with a flat panel detector of an angiography machine. The lower arm has six degrees of freedom, with an end portion fixedly provided with an anode ball tube of the angiography machine. According to a telecentric motion implementation, 45-degree isocentric detection within a plane of a specific point is realized through a second shaft, a third shaft and a fourth shaft, and 45-degree taper angle detection within a space range is realized through rotation of a first shaft. A fifth degree of freedom prevents installation error influences, and the upper arm has a sixth degree of freedom. The double-arm type robot and a three-degree-of-freedom mobile table body are arranged in a mobile ambulance body, the double-arm type robot realizes fixed-point and different-angle isocentric detection, and different positions can be detected by moving the table body. The third shaft is driven by gears and a rack to move in two directions, and in order to realize the function, one of the double gears is constantly engaged with the rack through belt transmission. Two high-precision guide rails are superimposed, which can not only realize high-precision motion, but also satisfy the requirements of bidirectional motion. The compact design of fourth or fifth degree of freedom can save space by reducing the overall height through pulleys and the gears. The sixth degree of freedom of the upper arm changes an isocentric distance between a receiver and a transmitter through belt transmission and ball screw transmission. The realization of the seven degrees of freedom of the upper arm is accomplished through bevel gear transmission, mainly to reduce the occupied height space. There are two ways to align the center by the ball tube fixed to the upper arm and the flat panel detector fixed to the lower arm, one is to use a mapping instrument next to the upper arm and the lower arm to align the center, and the other is to receive, through the flat panel detector, X-rays emitted by the ball tube and then align the center according to parameters of light frame pixels on a panel. Large-scale isocentric detection is realized by cooperation of the isocentric motion of the upper arm and the lower arm and the up-down, left-right and front-back motion of the table, thereby providing high-quality angiograms in the minimally invasive surgery process.

FIG. 4 is a schematic diagram of the first shaft and the second shaft. The first shaft drives, by a motor, a second-shaft base to move, a crossed roller bearing supports the second-shaft base, the motor and a speed reducer are fixed to the second-shaft base, and a gas strut is used for reducing output torque of the motor and the speed reducer.

Figure 5A:
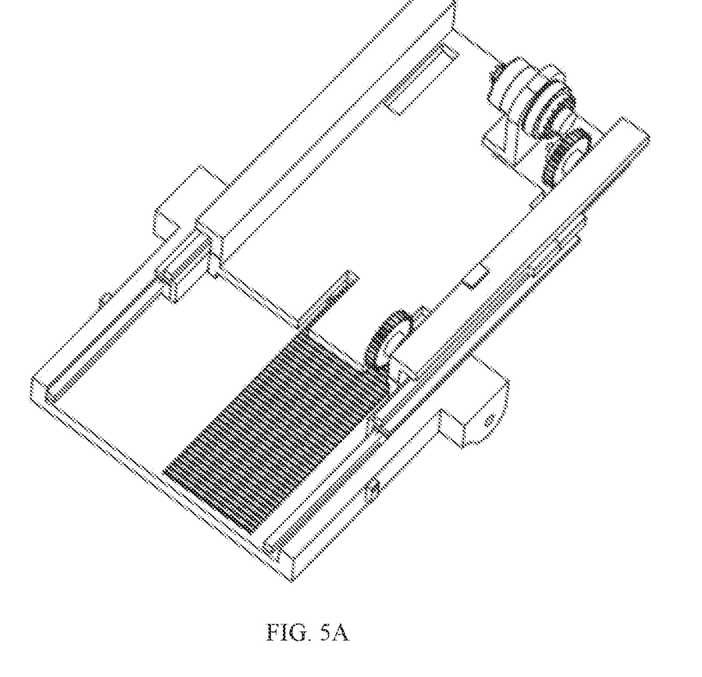
FIGS. 5A to 5D are schematic diagrams of a third joint of an upper arm and a lower arm according to the present invention.
Figure 5B:
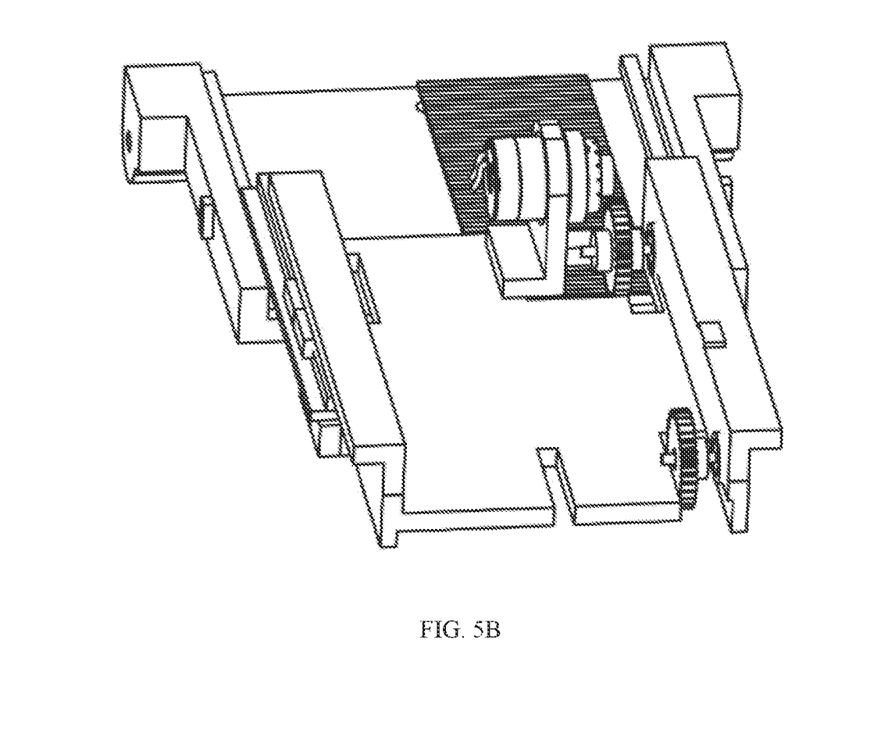
Figure 5C:
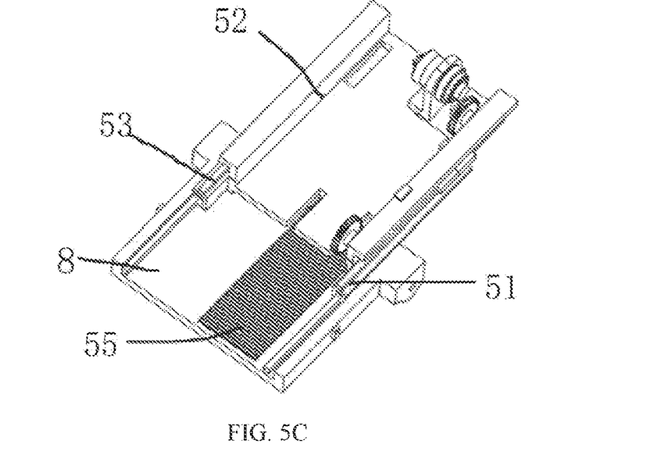
Figure 5D:
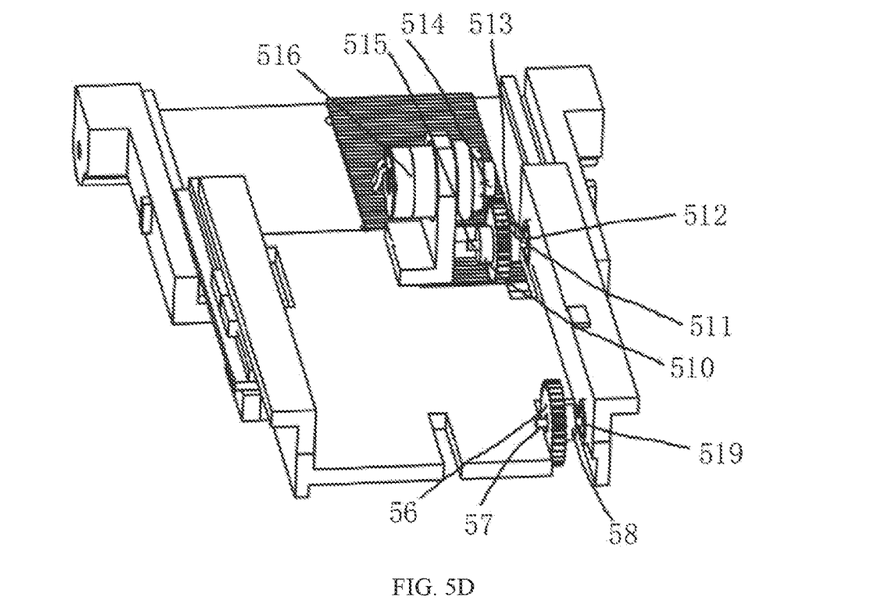

FIG. 5C is a schematic diagram of a third joint. The motor drives pulleys to transmit the motion to a gear, and then transmits the motion to the other gear through another pair of pulleys, the two gears synchronously move and are engaged with a lower rack, thereby realizing linear motion of the third shaft. The double gear setting is to ensure that there is constantly one gear kept in an engaged state during bidirectional motion. The FIG. above shows left and right limit states.

FIG. 6C illustrates a slide rail, slide block, connector, slide rail and slide block structure, which can realize bidirectional motion. The load is borne for the structure in FIG. 5C to ensure the motion precision.

In FIG. 7B, a fourth-shaft motor drives pulleys and is matched with a fifth-shaft motor to synchronously move so as to realize the pitching motion of a speed limiter and the ball tube, the fifth-shaft motor independently moves to drive the pulleys and transmits the motion to a bevel gear so as to control the sidesway motion of the speed limiter and the ball tube. The speed limiter performs spinning motion around an axis of the sixth shaft. A fourth shaft and a fifth shaft of the upper arm are identical to those of the lower arm in structure.

In FIG. 9, the motor transmits output torque to a belt pulley and then to a screw nut through a pulley, thereby realizing up-down motion.

In FIG. 10, the output torque of the motor is transmitted to a receiving panel through a bevel gear, thereby realizing rotating around the self axis.

Through the setting of above-mentioned degrees of freedom, the present invention can realize isocentric motion of the upper arm and the lower arm around the specific point, and can adjust the posture of plus or minus 45°; and in order to expand the detection range, a table moving mechanism can be controlled to realize the left-right and front-back motion of the table body, a detection area of 300 mm*300 mm can be realized as a whole, and the table body moves up and down through the table moving mechanism so as to adapt to the height difference of different surgeons, so that the height of the patient is in the best position relative to the surgeon.

It is to be understood that the above specific description of the present invention is only used to illustrate the present invention but is not limited to the technical solutions described in the embodiments of the present invention, and those of ordinary skill in the art should understand that the present invention can still be subjected to modifications or equivalent replacements so as to achieve the same technical effect; and as long as the requirements of use are satisfied, they are all within the scope of protection of the present invention.

What is claimed is:

1. A vehicle-mounted angiography machine with a double-robotic-arm type structure, comprising a six-degree-of-freedom robotic lower arm at a lower portion of an ambulance body space, a three-degree-of-freedom mobile table located in a middle of the ambulance body space for moving a patient, and a seven-degree-of-freedom robotic upper arm at an upper portion of the ambulance body space;

an end portion of the seven-degree-of-freedom robotic upper arm is connected to a flat panel detector of the vehicle-mounted angiography machine, and an end portion of the six-degree-of-freedom robotic lower arm is connected to an anode ball tube of the vehicle-mounted angiography machine; a central motion of the seven-degree-of-freedom robotic upper arm and the six-degree-of-freedom robotic lower arm is matched with a up-down, left-right and front-back motion of the three-degree-of-freedom mobile table;

each of the seven-degree-of-freedom robotic upper arm and the six-degree-of-freedom robotic lower arm comprises a six-degree-of-freedom module, the six-degree-of-freedom module of the six-degree-of-freedom robotic lower arm is provided with the anode ball tube, and the seven-degree-of-freedom robotic upper arm further comprises a seventh-shaft module arranged on the six-degree-of-freedom module;

the six-degree-of-freedom module comprises a first-second joint base, a third-joint module arranged on the first-second joint base, and a fourth-fifth-sixth-shaft module arranged on the third-joint module;

the first-second joint base comprises a first-shaft base and a second-shaft base arranged above the first-shaft base; the first-shaft base and the second-shaft base are connected through a crossed roller bearing, a pivot joint is rotationally connected in the first-shaft base, a first end of the pivot joint penetrates through the first-shaft base, with a penetrating-out end portion connected to a bottom of the second-shaft base, a second end of the pivot joint is driven by a pivot joint drive motor to rotate, and the second-shaft base is driven by the pivot joint to rotate accordingly; the third-joint module is arranged above the second-shaft base; and a gear motor is installed on the second-shaft base, and the gear motor is installed on the second-shaft base through a motor mounting plate;

the third-joint module comprises a third-shaft base, and a front portion of the third-shaft base and a front portion of the second-shaft base are connected through a pivot; the gear motor drives the pivot to rotate, a gas spring is arranged between a rear portion of the second-shaft base and a rear portion of the third-shaft base, a first end of the gas spring is hinged to the second-shaft base, and a second end of the gas spring is hinged to a bottom of the third-shaft base; the third-shaft base is provided with two parallel mobile guide rail and slide block modules, and a fourth-shaft base is in sliding connection to the third-shaft base through the bidirectional mobile guide rail and slide block modules; the third-shaft base is provided with a rack, and the fourth-shaft base is provided with a first gear and a second gear; the first gear and a first pulley are installed on a first third-shaft, and a second pulley, the second gear and a third pulley are installed on a second third-shaft; the first third-shaft is connected to the fourth-shaft base through a first mounted bearing, and the second third-shaft is connected to the fourth-shaft base through a second mounted bearing; the first pulley and the third pulley are connected through a first synchronous belt to form a first synchronous belt transmission structure; the fourth-shaft base is provided with a third-shaft joint module motor, a motor shaft of the third-shaft joint module motor is provided with a fourth pulley, and the fourth pulley and the second pulley constitute a second synchronous belt transmission structure through a second synchronous belt; the third-shaft joint module motor acts, the second pulley rotates and drives the second gear and the third pulley coaxial thereto to rotate together, the first pulley rotates through the first synchronous belt transmission structure to drive the first gear coaxial thereto to rotate, the first gear and the second gear are in meshing transmission with the rack to drive the fourth-shaft base to horizontally move along the two parallel mobile guide rail and slide block modules; and the bidirectional mobile guide rail and slide block module comprises a first-layer guide rail and a second-layer guide rail, wherein the first-layer guide rail is arranged on the third-shaft base to be connected to the third-shaft base; and a first-layer slide block is in sliding connection to the first-layer guide rail, a bottom of a guide rail connector is arranged on an upper surface of the first-layer slide block, an upper surface of the guide rail connector is provided with the second-layer guide rail, the second-layer guide rail is connected to a second-layer slide block, and the second-layer slide block is connected to the fourth-shaft base.

2. The vehicle-mounted angiography machine with the double-robotic-arm type structure according to claim 1, wherein the second gear is located between the second pulley and the third pulley, and the third-shaft joint module motor is installed on the fourth-shaft base through a third-shaft joint module motor base.

3. The vehicle-mounted angiography machine with the double-robotic-arm type structure according to claim 2, wherein the fourth-shaft base is provided with the fourth-fifth-sixth-shaft module, wherein the fourth-fifth-sixth-shaft module comprises a fourth-shaft module, a fifth-shaft module and a sixth-shaft module;

the fourth-shaft module comprises a first synchronous belt structure constituted by a first fourth-shaft pulley and a second fourth-shaft pulley, and the first fourth-shaft pulley of the first synchronous belt structure is driven by a fourth-shaft motor; and the second fourth-shaft pulley serves as a first driven pulley to be installed on a fourth-shaft driven shaft, and the fourth-shaft driven shaft is fixed to a fourth-shaft holder through a fourth-shaft mounted bearing, and the fourth-shaft driven shaft is further connected to a first side of a fifth-shaft connector;

the fifth-shaft module comprises a second synchronous belt structure constituted by a first fifth-shaft pulley and a second fifth-shaft pulley, and the first fifth-shaft pulley of the second synchronous belt structure is driven by a fifth-shaft motor; the second fifth-shaft pulley serves as a second driven pulley to be installed on a fifth-shaft driven shaft, and the fifth-shaft driven shaft is fixed to a fifth-shaft holder through a fifth-shaft mounted bearing, and the fifth-shaft driven shaft is further connected to a second side of the fifth-shaft connector; and the fifth-shaft driven shaft is further provided with a first fifth-shaft gear, the first fifth-shaft gear is connected to a second fifth-shaft gear through meshing transmission, the second fifth-shaft gear is installed on a fifth-shaft gear shaft, and the fifth-shaft gear shaft is installed on the fifth-shaft connector through a fifth-shaft crossed roller bearing.

4. The vehicle-mounted angiography machine with the double-robotic-arm type structure according to claim 3, wherein in the six-degree-of-freedom robotic lower arm, the fifth-shaft crossed roller bearing is connected to the anode ball tube through a connecting rod; and the fourth-shaft motor is matched with the fifth-shaft motor to synchronously move, thereby realizing a pitching motion of the fifth-shaft connector; and when the fifth-shaft motor independently moves, the pulley is driven to transmit a motion to the second fifth-shaft gear.

5. The vehicle-mounted angiography machine with the double-robotic-arm type structure according to claim 4, wherein the sixth-shaft module comprises a sixth-shaft holder installed on a crossed roller bearing, a sixth-shaft screw is fixed to the sixth-shaft holder, a sixth-shaft nut is fixed to the sixth-shaft screw, the sixth-shaft nut is connected to a sixth-shaft adapter, the sixth-shaft adapter is arranged on a sixth-shaft slide block, the sixth-shaft slide block is in sliding connection to a sixth-shaft guide rail, the sixth-shaft guide rail is arranged on the sixth-shaft holder, the sixth-shaft screw is configured to rotate relative to the sixth-shaft holder, and the sixth-shaft screw is parallel to the sixth-shaft guide rail;

one end portion of the sixth-shaft screw is provided with a first sixth-shaft pulley, the first sixth-shaft pulley and a second sixth-shaft pulley constitute a third synchronous belt structure, the third synchronous belt structure is driven by a sixth-shaft motor, and the sixth-shaft motor is fixed to the sixth-shaft holder through a sixth-shaft motor base.

6. The vehicle-mounted angiography machine with the double-robotic-arm type structure according to claim 5, wherein in the seven-degree-of-freedom robotic upper arm, the sixth-shaft nut is connected to a receiving panel through a seventh-shaft holder, a first end of the seventh-shaft holder is connected to the sixth-shaft nut, and a second end of the seventh-shaft holder is provided with the receiving panel; a lower end of the receiving panel is rotationally connected to the seventh-shaft holder through a seventh-shaft driven shaft, the seventh-shaft driven shaft is rotationally connected to the seventh-shaft holder through a seventh-shaft crossed roller bearing, an end portion of the seventh-shaft driven shaft is externally provided with a second bevel gear, the second bevel gear is connected to a first bevel gear through meshing transmission, the first bevel gear is installed outside a motor shaft of a seventh-shaft motor, and the seventh-shaft motor is installed on the seventh-shaft holder through a seventh-shaft motor base.

* * * * *